United States Patent [19]

Haramaki et al.

[11] Patent Number: 5,371,280

[45] Date of Patent: Dec. 6, 1994

[54] POLYMERIZATION INHIBITOR AND INHIBITING METHOD FOR VINYL COMPOUND

[75] Inventors: Hidefumi Haramaki; Kazuhiko Sakamoto; Masatoshi Ueoka; Yohji Akazawa; Masao Baba, all of Hyogo, Japan

[73] Assignee: Nippon Shokubai Co., Ltd., Osaka, Japan

[21] Appl. No.: 788,326

[22] Filed: Nov. 5, 1991

[30] Foreign Application Priority Data

| Nov. 9, 1990  | [JP] | Japan | 2-305058 |
| Nov. 10, 1990 | [JP] | Japan | 2-304860 |
| May 10, 1991  | [JP] | Japan | 3-105926 |
| Jun. 14, 1991 | [JP] | Japan | 3-143585 |

[51] Int. Cl.$^5$ ............................ C07C 57/04; B01D 3/34
[52] U.S. Cl. ........................................ 562/26; 567/27; 567/28; 564/76; 203/8; 203/9; 252/380; 252/389.53; 252/400.53
[58] Field of Search ............... 564/76; 203/8, 9; 562/27, 28; 252/380, 389.53, 400.53

[56] References Cited

U.S. PATENT DOCUMENTS

| 2,829,152 | 4/1953  | Garret et al. |         |
| 2,977,345 | 3/1961  | Fischer et al. | 562/27 |
| 3,248,400 | 4/1966  | Flies et al. | 562/27 |
| 3,322,802 | 5/1967  | Brooks et al. | 562/27 |
| 3,390,198 | 6/1968  | Leston et al. | 562/598 |
| 3,879,343 | 4/1975  | DeBrunner et al. | 564/76 |
| 4,061,595 | 12/1977 | Watson | 203/9 |
| 4,348,515 | 9/1982  | Morgan | 564/76 |
| 4,621,310 | 5/1977  | Shimizu et al. | 203/8 |
| 4,663,480 | 5/1987  | Inskip et al. | 562/598 |

FOREIGN PATENT DOCUMENTS

| 57-61015  | of 0000 | Japan . |       |
| 4866575   | 12/1971 | Japan | 203/8 |
| 61-176672 | 8/1986  | Japan . |       |

OTHER PUBLICATIONS

Chemical Abstracts, vol. 90, No. 10, issued 1978 (Columbus, Ohio, USA) Standner, E. et al., "Effect of Organic Sulfur Compounds on the Polymerization of Vinyl Monomers", (Abstract enclosed), Abstract No. 72531e, Zb. Chemickotechnol. Fak, vol. Date 1975–1976 177–87 (Slo.).

Primary Examiner—Marianne M. Cintins
Assistant Examiner—Keith Ma Millan
Attorney, Agent, or Firm—Lowe, Price, LeBlanc & Becker

[57] ABSTRACT

This invention is directed to a polymerization inhibitor and a polymerization inhibiting method which enables the continuous operation of a device for producing vinyl compounds over a long period of time and virtually eliminates corrosion. Further, the polymerization inhibitors according to the present invention are superior in polymerization inhibition when transferring and storing the vinyl compound products and in other cases. The polymerization inhibitor according to the present invention contains manganese dithiocarbamate or a thiuram compound as an effective component. The polymerization inhibiting method of this invention comprises individual or joint use of said inhibitors, or joint use of a copper salt, another manganese salt, or quinones in addition to said inhibitors. Further, the method may comprise jointly using copper dithiocarbamates in a manganese salt as polymerization inhibitors, or jointly using quinones in addition to the salts.

17 Claims, No Drawings

POLYMERIZATION INHIBITOR AND INHIBITING METHOD FOR VINYL COMPOUND

BACKGROUND OF THE INVENTION

The present invention relates to a polymerization inhibitor and a polymerization-inhibiting method for a vinyl compound.

The vinyl compound generally has easily polymerizable properties by light and heat, etc. Therefore, to prevent the polymerization of a vinyl compound, various kinds of polymerization inhibitors are used alone or in combination with other polymerization inhibitors in accordance with the surrounding conditions of the vinyl compound.

An example of a particularly highly polymerizable vinyl compound includes (meth)acrylic acid. Hereinafter, in this specification, (meth)acrylic acid indicates both methacrylic acid and acrylic acid.

Hitherto, as methods for producing (meth)acrylic acid, there have been frequently used, for example, a method for producing acrylic acid by a catalytic gas phase oxidation reaction of propylene and/or acrolein, and a method for producing methacrylic acid by a catalytic gas phase oxidation reaction of isobutylene and/or methacrolein, etc.

In these methods, gas produced from the catalytic gas phase oxidation reaction is cooled and collected by water to obtain an aqueous solution of (meth)acrylic acid containing such by-products as acetic acid and an aldehyde, etc. and, from this aqueous solution, (meth)acrylic acid is separated and purified by combining processes such as distillation and extraction by a solvent. The method for producing (meth)acrylic acid by the forementioned catalytic gas phase oxidation reaction involves a process to separate, enrich, and purify, etc. the acid by distillation. Also, as methods for producing (meth)acrylic acid other than the above-described, there have been known a method for producing acrylic acid by Reppe's method and a method for producing methacrylic acid by the acetone cyanhydrin method, etc. In these methods there has been involved a process to separate, enrich, and purify (meth)acrylic acid by distillation.

The (meth)acrylic acid is very easily polymerized by light and heat, etc. Therefore, the polymerizing properties of (meth)acrylic acid increases, especially, under high temperature conditions such as in the forementioned distillation process. Accordingly, when highly polymerizable (meth)acrylic acid like the forementioned is industrially produced, polymerization of these acids in a distillation process is a very important item in operation of the process. Further, to establish an effective polymerization-preventive art in a distillation process the acid under a high temperature is an essentially important item for operating the process continuously for a long period of time and under a stable condition. According to the knowledge of present inventors, the polymerization most easily takes place in a dehydrating process (a water-separating process) during the forementioned distillation course and this fact is a main factor which disturbs continuous operations of a production device including a distillation column.

When subjecting (meth)acrylic acid to operations such as separation, enriching, and purification using a distillation column, most of the places where a polymerization product is easily formed by a polymerization reaction of the acid are areas with scarce wetting by liquid such as a rear side of a tray, an inside of bubble cap, a rear side of a downcomer, a hollow on a column inside, etc. and a place of easily liquid-stagnating such as a metal fittings (bolt and nut, etc.) for putting-in a tray and a packing part, etc. The polymerization product is hardly soluble in (meth)acrylic acid, water, and usual organic solvents and, once formed in a column, it becomes a seed for polymerization and gradually accumulates. Finally, the column inside is clogged by it and a continuous operation of the production device becomes impossible. Further, it is very difficult to remove these accumulated polymerization products.

Conventionally, a method of carrying out distillation in the presence of a polymerization inhibitor has been adopted as a measure for preventing polymerization of (meth)acrylic acid in a distillation process when producing (meth)acrylic acid. As polymerization inhibitors of this kind, is hitherto known a polymerization inhibitor (A) composed of the following ingredients: at least one kind of compound selected from the group consisting of hydroquinone, methoquinone (p-methoxyphenol), cresol, phenol, tertiary-butylcatechol, diphenylamine, phenothiazine, and methylene blue, at least one kind of copper dithiocarbamate selected from the group consisting of copper dimethyldithiocarbamate, copper diethyldithiocarbamate, and copper dibutyldithiocarbamate, and molecular oxygen (for acrylic acid, refer to Japanese Official Patent Provisional Publication, showa 49-85016; for methacrylic acid, refer to Japanese Official Patent Gazette, showa 57-61015). Hitherto-known polymerization inhibitors of (meth)acrylic acid other than the above are a polymerization inhibitor (B-1) composed of a manganese salt such as manganese acetate etc., a polymerization inhibitor (B-2) composed of a manganese salt such as manganese acetate etc. with hydroquinone and/or methoquinone, a polymerization inhibitor (B-3) composed of a manganese salt such as manganese acetate etc. with molecular oxygen, and a polymerization inhibitor (B-4) composed of a manganese salt such as manganese acetate etc., hydroquinone and/or methoquinone, and molecular oxygen (for all of these, refer to Japanese Official Patent Provisional Publication, showa 51-98211).

However, the inventors examined polymerization-inhibiting effects of the above-mentioned known polymerization inhibitors of (A) and from (B-1) to (B-4), so that the inventors found that the polymerization inhibitors of (A) and from (B-1) to (B-4) have the following problems.

That is, the polymerization inhibitor (A) disclosed in the Japanese Official Patent Provisional Publication, showa 49-85016 and Japanese Official Patent Gazette, showa 57-61015, has low polymerization-inhibiting effects when polymerization of (meth)acrylic acid very easily occurs by containing water, acetic acid, and aldehyde compounds in the feed composition as in an azeotropic separation column (a water-separating column) of an aqueous (meth)acrylic acid solution in the distillation process, when (meth)acrylic acid is produced by a catalytic gas phase oxidation reaction. Due to the low inhibiting effect, there was a problem that, with generation of a popcorn polymer and a sticky polymer in the course of distillation, continuous operation in a long period of time of a production device including a distillation column became impossible. Also, since this polymerization inhibitor (A) contains a copper salt having a corrosive character, there is a problem that the distillation column easily corrodes during a continuous operation in a long period of time.

On the other hand, the polymerization inhibitors of from (B-1) to (B-4) disclosed in the Japanese Official Patent Provisional Publication, showa 51-98211, contains a manganese salt having a low corrosive character, so that there is no problem about corrosion of the distillation column. The polymerization inhibitors of from (B-1) to (B-4) have sufficient polymerization-inhibiting effects on the products from (meth)acrylic acid, but the polymerization-inhibiting effects is insufficient, similarly to the case of the polymerization-inhibitor (A), in a case where polymerization of (meth)acrylic acid very easily occurs as in an azeotropic separation column of an aqueous (meth)acrylic acid solution in the distillation process, when (meth)acrylic acid is produced by a catalytic gas phase oxidation reaction. Thus, there was a problem that, with generation of a popcorn polymer and a sticky polymer during distillation, continuous operation over a long period of time in a production device became impossible.

Also, there were problems similar to the forementioned in the conventional polymerization inhibitors and polymerization-inhibiting methods of a vinyl compound other than (meth)acrylic acid.

SUMMARY OF THE INVENTION

Under these circumstances, an object of the present invention is to provide a polymerization inhibitor and a polymerization-inhibiting method both of which make continuous operation of a device for producing vinyl compounds, i.e., monomers, over in a long period of time possible and make corrosion of the device quite small, and also, are superior in polymerization inhibition in case of transferring and storing the vinyl compound products and in other cases.

To solve the forementioned object, the present inventors carried out extensive studies. As a result, the inventors' experiments led to a finding that, if a dithiocarbamic acid manganese salt or a thiuram compound which is explained later in detail is used as an effective ingredient being involved in the polymerization inhibitor, the polymerization-inhibiting effects greatly increase when compared with the forementioned conventional polymerization inhibitors, so that continuous operation of a production device in a long period of time becomes possible, and also, corrosion of the device becomes quite small. Thus, the present invention was completed.

Therefore, first, a polymerization inhibitor for a vinyl compound relating to the present invention comprises, as an effective component, at least one kind of dithiocarbamic acid manganese salts, in which two hydrocarbon groups of an identical kind or each other different kinds selected from the group consisting of a methyl group, an ethyl group, a propyl group, a butyl group, and a phenyl group are bonded with the nitrogen atom. The propyl group or butyl group may be a straight chain type or may be a branch type (hereinafter, this compound is simply referred to as "manganese dithiocarbamate").

Secondly, a polymerization inhibitor for a vinyl compound relating to the present invention may comprise, as an effective component, a thiuram (thiocarbamoyl) derivative represented by the following general formula (1) (hereinafter, this is simply referred to as "thiuram compound").

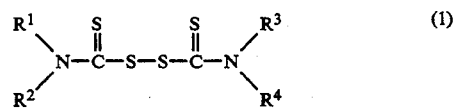

(But, $R^1$, $R^2$, $R^3$, and $R^4$ independently denote any one of an alkyl group having the carbon number of 1 to 8 and a phenyl group.)

The thiuram compounds used in the present invention are practically exemplified by tetramethylthiuram disulfide, tetraethylthiuram disulfide, tetrapropylthiuram disulfide, tetrabutylthiuram disulfide, tetraoctylthiuram disulfide, tetraphenylthiuram disulfide, and the like.

First, a polymerization-inhibiting method for a vinyl compound relating to the present invention involves a use of the polymerization inhibitor comprising the forementioned manganese dithiocarbamate (hereinafter, this method is referred to as "the first polymerization-inhibiting method").

Secondly, a polymerization-inhibiting method for a vinyl compound relating to the present invention may involve the use of the polymerization inhibitor comprising the forementioned thiuram compound (hereinafter, this method is referred to as "the second polymerization-inhibiting method").

A polymerization-inhibiting method for a vinyl compound relating to the present invention is not limited to the above-described ones. That is, in the course of the forementioned extensive studies, the inventors have confirmed by experiments that, if a copper dithiocarbamate and a manganese salt are jointly used as polymerization inhibitors, the amount for use of the copper dithiocarbamate having high corrosive property can be reduced and corrosion of the production device by the copper dithiocarbamate is depressed.

Therefore, thirdly, a polymerization-inhibiting method for a vinyl compound relating to the present invention may comprise the joint use of a copper dithiocarbamate and a manganese salt as polymerization inhibitors (hereinafter, this method is referred to as "the third polymerization-inhibiting method").

In the first polymerization-inhibiting method of this invention, sufficiently superior polymerization-inhibiting effects can be obtained even if it comprises a use of a polymerization inhibitor only containing a manganese dithiocarbamate, but if necessary, it is possible jointly to use at least one kind selected from a group consisting of a copper salt and a manganese salt other than a manganese dithiocarbamate (hereinafter, this is simply referred to as "the other manganese salt") as the polymerization inhibitor as well. In this case, further superior polymerization-inhibiting effects can be obtained.

Similarly, also in the second polymerization-inhibiting method of this invention, if necessary, in addition to the thiuram compound, it is possible jointly to use at least one kind selected from a group consisting of a manganese salt and a copper salt as the polymerization inhibitor. In this case, further superior polymerization-inhibiting effects can be obtained.

Preferable examples of the other manganese salt which is, if necessary, used in the first polymerization-inhibiting method of the present invention may be either organic or inorganic salts and they are not especially limited. However, as the preferable organic salts are cited saturated or unsaturated manganese carboxylates having the carbon number of 1 to 8 such as manganese formate, manganese acetate, manganese octanate, etc.; other manganese carboxylates such as manganese naphthenates etc.; and the like. And as the preferable inorganic salts are cited potassium permanganate etc.

Preferable examples of a manganese salt which is, used in the second and third polymerization-inhibiting methods of the present invention are not especially limited. However, for example, are cited the manganese dithiocarbamates and the other manganese salts as forementioned, and so on.

Although copper salts which are, if necessary, used in the first or second polymerization-inhibiting method of the present invention are not especially limited, their preferable examples are copper dithiocarbamate such as copper dimethyldithiocarbamate, copper diethyldithiocarbamate, copper dipropyldithiocarbamate, copper dibutyldithiocarbamate, copper diphenyldithiocarbamate, etc. Besides them, are also cited saturated or unsaturated copper carboxylates having the carbon number of 1 to 8 such as copper acetate, copper octanate, etc.; and the like.

The forementioned salts of manganese and copper are used alone or jointly used in a plural kind.

In the first, second, and third polymerization-inhibiting methods, in case of necessity, if benzene derivatives such as hydroquinone etc. or molecular oxygen are jointly used in addition to the forementioned polymerization inhibitors which are individually or jointly used, because of synergistic effect of these polymerization inhibitors, the polymerization-inhibiting effects greatly increase when compared with the forementioned conventional polymerization-inhibiting methods, and continuous operation of a production device for a long period of time becomes possible. As the forementioned benzene derivatives, besides hydroquinone, are cited methoquinone (p-methoxyphenol), cresol, phenol, tertiary-butylcatechol, diphenylamine, phenothiazine, methylene blue, etc. It is specially preferable to use hydroquinone and/or methoquinone among said benzene derivatives.

The vinyl compound to which the polymerization inhibitor and the polymerization-inhibiting method of this invention are applicable is not especially limited. But, for example, an acrylic acid ester, methacrylic acid ester, acrylonitrile, styrene, etc. are cited besides the (meth) acrylic acid.

An application range of the polymerization inhibitor and the polymerization-inhibiting method of this invention is not especially limited. For example, a reaction vessel, distilling column, condensation column, a storage tank of a purified vinyl compound, etc. are applied. Practically, if the case producing (meth)acrylic acid by a catalytic gas phase oxidation reaction is explained, an effective application is coexisting of the present invention's polymerization inhibitor with (meth)acrylic acid in various processes, including various distillation processes such as a rectifying column of (meth)acrylic acid, a separation column between (meth)acrylic acid and a solvent, a separation column between (meth)acrylic acid and a light portion such as acetic acid, etc. and also, which include a distillation operation of stripper etc. of a light portion such as acrolein, methacrolein, etc.

In the polymerization-inhibiting method of this invention, each polymerization-inhibiting component is usually used by adding it into a vinyl compound or a solution of this. This adding method is not especially limited. For example, since a manganese dithiocarbamate or a thiuram compound is easily soluble in a vinyl compound, it may be directly added in form of a solid, a powder, etc., or may be added in form of a solution by dissolving it into a proper organic solvent. Also, other polymerization-inhibiting components, according to the kind, may be directly added in form of a solid, a powder, etc., or may be added in form of a solution in which they are dissolved into a proper organic solvent. Besides, molecular oxygen which is used in case of necessity may be directly mingled into a vinyl compound or a solution of this by an air-bubbling method, etc., or may be indirectly mingled into a vinyl compound or a solution of this in form of a solution of the other polymerization-inhibiting component in which molecular oxygen is dissolved.

The time of adding each polymerization-inhibiting component is not especially limited. It may be separately added to the vinyl compound or a solution of this, or may be added at one time, for example, in form of one solution.

Practically, for example, in a distillation process in producing (meth)acrylic acid, since polymerization-inhibiting components other than molecular oxygen are relatively soluble in (meth)acrylic acid as well as in an organic solvent being used in the process for producing these acids, they may be introduced in the process by dissolving them in a supplying solution or in a reflux solution. Also, molecular oxygen may be transferred in a gas form from the bottom of a distillation column or that of a separation column and/or from a reboiler.

In the first or second polymerization-inhibiting method for vinyl compounds relating to the present invention, amount of polymerization inhibitor used generally varies with the composition of a polymerization inhibitor (the kind of combining ingredients in a polymerization inhibitor), operation conditions, etc., and it is not especially limited. For example, in a case where the manganese dithiocarbamate or thiuram compound is used alone, its preferable adding amount is from 10 to 50 ppm (weight standard) against a boiling up amount of a vinyl compound. Furthermore, in a case where the manganese salt (the manganese salt other than the manganese dithiocarbamate in case of the first polymerization-inhibiting method) or copper salt (B) is jointly used in addition to the manganese dithiocarbamate or thiuram compound (A), it is preferred that a total adding amount of these compounds (A+B) is adjusted at from 10 to 100 ppm (weight standard) against a boiling up amount of a vinyl compound. Furthermore, in a case where the manganese salt (the manganese salt other than the manganese dithiocarbamate in case of the first polymerization-inhibiting method) or copper salt (B) and the benzene derivative such as hydroquinone, methoquinone, etc. (C) are jointly used in addition to the manganese dithiocarbamate or thiuram compound (A), it is preferred that a total adding amount of these compounds (A+B+C) is adjusted at from 10 to 500 ppm (weight standard) against a boiling up amount of a vinyl compound. Also, in a case where a polymerization-inhibiting method of the present invention is carried out, if the method is carried out in the presence of molecular oxygen, the effects lasts. Therefore, it is preferable to pour molecular oxygen in amount of from about 0.05 to 0.5% by volume against a boiling up amount of a vinyl compound.

The amount of copper dithiocarbamates and manganese salts used in the third polymerization-inhibiting method and the benzene derivative such as hydroquinone, methoquinone, etc. and molecular oxygen used in case of necessity varies depending upon the kind polymerization inhibitors used and operation conditions, and it is not especially limited. However, for example, it is preferred that a total adding amount ($x_1+x_2+x_3$) of the copper dithiocarbamate ($x_1$), manganese salt ($x_2$), and benzene derivative ($x_3$) is adjusted at 20 to 500 ppm (weight standard) against a boiling up amount of a vinyl compound and an amount of pouring molecular oxygen is adjusted at 0.05 to 0.5% by volume against a boiling up amount of a vinyl compound. Additionally, the ratio of the manganese salt to the copper dithiocarbamate used is not especially limited, but it is preferred that the weight ratio (Mn/Cu) of the manganese atom in the manganese salt to the copper atom in the copper dithiocarbamate is adjusted in a range of from about 1 to 10 and, more preferred that it is adjusted in a range of from about 2 to 4. In a case where the Mn/Cu ratio is less than 1, a problem of the device's corrosion according to operating conditions takes place and, in a case where the ratio exceeds 10, the polymerization-inhibiting effect is not sufficient.

If formulated so as to contain a manganese dithiocarbamate or a thiuram compound as an effective ingredient, the polymerization-inhibiting effects are much increased when compared with those of conventional polymerization inhibitors and, because polymerization of a vinyl compound is sufficiently prevented even under a condition wherein the vinyl compound easily polymerizes, continuous operation over a long period in time of a device for producing the vinyl compound, which includes a distillation column of the vinyl compound, becomes possible, and the superior polymerization-inhibiting effects are also displayed in case of transferring and storing the vinyl compound products and in other cases. Furthermore, since the manganese dithiocarbamate and the thiuram compound have only a very weak corrosive property, corrosion of the production device is slight.

Further, when a copper dithiocarbamate and a manganese salt are jointly used as polymerization inhibitors, similarly as forementioned, the polymerization of a vinyl compound is sufficiently prevented by a synergistic effect of the above polymerization inhibitors. Because of this, it is possible continuously to operate a device for producing the vinyl compound over a long period of time, and the superior polymerization-inhibiting effects are also displayed when transferring and storing the vinyl compound products and in other cases. Furthermore, since the manganese salt weakens the corrosive property of the copper dithiocarbamate, corrosion of the device becomes small.

Thus, according to the polymerization inhibitor and polymerization-inhibiting method for a vinyl compound relating to the present invention, the polymerization of a vinyl compound is sufficiently prevented even under the conditions that the vinyl compound easily undergoes polymerization, and thereby, continuous operation over a long period of time in a device for producing the vinyl compound, which includes a distillation column of the vinyl compound, becomes possible, and also, corrosion of the device is slight. Also, the polymerization inhibitor and polymerization-inhibiting method for a vinyl compound are applicable not only when producing the vinyl compound, but also when transferring and storing the product of the compound and in other cases.

DESCRIPTION OF THE PREFERRED EMBODIMENTS

Hereinafter, practical examples and comparative examples of the present invention are shown together, but the present invention is not limited to the undermentioned examples. The unit "ppm" in the examples and comparative examples are by weight.

EXAMPLE 1.1

An acrylic acid solution was prepared by adding manganese dibutyldithiocarbamate as a polymerization inhibitor in a proportion of 1 ppm to purified acrylic acid (a vinyl compound).

Next, in order to eliminate the effect of molecular oxygen upon the polymerization-inhibiting effect to analyze only the polymerization-inhibiting effect by manganese dibutyldithiocarbamate, 5 ml of the acrylic acid solution was taken into a 20 ml test tube, oxygen dissolved in the acrylic acid solution was removed by bubbling a nitrogen gas for 1 minute with a stream amount of 30 ml/minute, and the test tube was sealed.

This test tube was immersed in an oil bath maintained at 130° C. and a polymerization-initiating time of acrylic acid was measured. This time is the time from immersing a test tube in an oil bath until getting turbidity in the solution sealed in the test tube. Results are shown in the following Table 1.1

EXAMPLES 1.2 TO 1.16 AND COMPARATIVE EXAMPLES 1.1 TO 1.23

The procedure of Example 1.1 was repeated except that the kind of vinyl compounds, the kind and adding amount of polymerization-inhibitors, the heating temperature, and addition of a polymerization initiator (AIBN: azoisobutyronitrile) are varied as shown in the following Tables 1.1 to 1.8, whereby the polymerization-initiating time of vinyl compounds was measured and the results are shown in the Tables 1.1 to 1.8.

Additionally, in the following Tables 1.1 to 1.8, the "none" in the column "joint use of molecular oxygen", as in the example 1.1, means that the effect of molecular oxygen upon the polymerization-inhibiting effect is removed by bubbling of a nitrogen gas into a solution of a vinyl compound for 1 minute with a stream of 30 ml/minute, and the "yes" in the same column means that the molecular oxygen was together used as a polymerization inhibitor by bubbling of air instead of a nitrogen gas into the solution for 1 minute with a stream of 30 ml/minute.

TABLE 1.1

| | vinyl compound | polymerization inhibitor solid portion kind | adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.1 | acrylic acid | manganese dibutyldithiocarbamate | 1 | none | 0 | 130 | 26 |
| comparative | acrylic | manganese acetate | 1 | none | 0 | 130 | 17 |

TABLE 1.1-continued

| | vinyl compound | polymerization inhibitor solid portion kind | adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.1 | acrylic acid | | | | | | |
| example 1.2 | acrylic acid | manganese dibutyldithiocarbamate and hydroquinone | 1 50 | none | 0 | 130 | 75 |
| comparative example 1.2 | acrylic acid | manganese acetate and hydroquinone | 1 50 | none | 0 | 130 | 24 |
| example 1.3 | acrylic acid | manganese dibutyldithiocarbamate | 1 | yes | 0 | 130 | 71 |
| comparative example 1.3 | acrylic acid | copper dibutyldithiocarbamate | 1 | yes | 0 | 130 | 22 |

*(footnote): value (weight standard) against vinyl compound.

TABLE 1.2

| | vinyl compound | polymerization inhibitor solid portion kind | adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.4 | acrylic acid | manganese dibutyldithiocarbamate and copper acetate | 1 1 | yes | 0 | 130 | 84 |
| comparative example 1.4 | acrylic acid | manganese acetate | 1 | yes | 0 | 130 | 50 |
| example 1.5 | acrylic acid | manganese acetate and copper dibutyldithiocarbamate | 1 1 | yes | 0 | 130 | 72 |
| comparative example 1.5 | acrylic acid | hydroquinone | 50 | yes | 0 | 130 | 5 |
| comparative example 1.6 | acrylic acid | methoquinone | 50 | yes | 0 | 130 | 5 |
| comparative example 1.7 | acrylic acid | phenothiazine | 5 | yes | 0 | 130 | 22 |

*(footnote): value (weight standard) against vinyl compound.

TABLE 1.3

| | vinyl compound | polymerization inhibitor solid portion kind | adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.6 | acrylic acid | manganese dibutyldithiocarbamate and hydroquinone | 1 50 | yes | 0 | 130 | 200 or more |
| comparative example 1.8 | acrylic acid | copper dibutyldithiocarbamate and hydroquinone | 1 50 | yes | 0 | 130 | 50 |
| example 1.7 | acrylic acid | manganese dibutyldithiocarbamate copper acetate, and hydroquinone | 1 1 50 | yes | 0 | 130 | 200 or more |
| comparative example 1.9 | acrylic acid | manganese acetate and hydroquinone | 1 50 | yes | 0 | 130 | 81 |

*(footnote): value (weight standard) against vinyl compound.

TABLE 1.4

| | vinyl compound | polymerization inhibitor solid portion kind | polymerization inhibitor solid portion adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.8 | methacrylic acid | manganese dibutyldithiocarbamate | 1 | none | 0 | 160 | 35 |
| comparative example 1.10 | methacrylic acid | manganese acetate | 1 | none | 0 | 160 | 20 |
| example 1.9 | methacrylic acid | manganese dibutyldithiocarbamate and hydroquinone | 1 50 | none | 0 | 160 | 81 |
| comparative example 1.11 | methacrylic acid | manganese acetate and hydroquinone | 1 50 | none | 0 | 160 | 29 |

*(footnote): value (weight standard) against vinyl compound.

TABLE 1.5

| | vinyl compound | polymerization inhibitor solid portion kind | polymerization inhibitor solid portion adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.10 | methacrylic acid | manganese dibutyldithiocarbamate | 1 | yes | 0 | 160 | 85 |
| comparative example 1.12 | methacrylic acid | copper dibutyldithiocarbamate | 1 | yes | 0 | 160 | 26 |
| comparative example 1.13 | methacrylic acid | manganese acetate | 1 | yes | 0 | 160 | 63 |
| comparative example 1.14 | methacrylic acid | hydroquinone | 50 | yes | 0 | 160 | 5 |
| comparative example 1.15 | methacrylic acid | methoquinone | 50 | yes | 0 | 160 | 5 |
| comparative example 1.16 | methacrylic acid | copper dibutyldithiocarbamate and phenothizaine | 1 5 | yes | 0 | 160 | 30 |

*(footnote): value (weight standard) against vinyl compound.

TABLE 1.6

| | vinyl compound | polymerization inhibitor solid portion kind | polymerization inhibitor solid portion adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.11 | methacrylic acid | manganese dibutyldithiocarbamate and hydroquinone | 1 50 | yes | 0 | 160 | 200 or more |
| comparative example 1.17 | methacrylic acid | copper dibutyldithiocarbamate and hydroquinone | 1 50 | yes | 0 | 160 | 74 |
| comparative example 1.18 | methacrylic acid | manganese acetate and hydroquinone | 1 50 | yes | 0 | 160 | 102 |

*(footnote): value (weight standard) against vinyl compound.

TABLE 1.7

| | vinyl compound | polymerization inhibitor solid portion kind | polymerization inhibitor solid portion adding amount (ppm)* | joint use of molecular oxygen | adding amount of polymerization initiator (AIBN) (ppm)* | heating temperature (°C.) | polymerization initiating time (minutes) |
|---|---|---|---|---|---|---|---|
| example 1.12 | methyl acrylate | manganese dibutyldithiocarbamate and hydroquinone | 1 10 | yes | 0 | 100 | 200 or more |

TABLE 1.7-continued

| | | polymerization inhibitor | | adding amount of | | |
| | | solid portion | joint use | polymerization | | polymerization |
| | vinyl compound | kind | adding amount (ppm)* | of molecular oxygen | initiator (AIBN) (ppm)* | heating temperature (°C.) | initiating time (minutes) |
|---|---|---|---|---|---|---|---|
| comparative example 1.19 | methyl acrylate | hydroquinone | 10 | yes | 0 | 100 | 80 |
| example 1.13 | octyl acrylate | manganese dibutyldithiocarbamate and hydroquinone | 1 / 10 | yes | 1000 | 70 | 200 or more |
| comparative example 1.20 | octyl acrylate | hydroquinone | 10 | yes | 1000 | 70 | 90 |
| example 1.14 | methyl methacrylate | manganese dibutyldithiocarbamate and hydroquinone | 1 / 10 | yes | 200 | 80 | 200 or more |
| comparative example 1.21 | methyl methacrylate | hydroquinone | 10 | yes | 200 | 80 | 100 |

*(footnote): value (weight standard) against vinyl compound.

TABLE 1.8

| | | polymerization inhibitor | | adding amount of | | |
| | | solid portion | joint use | polymerization | | polymerization |
| | vinyl compound | kind | adding amount (ppm)* | of molecular oxygen | initiator (AIBN) (ppm)* | heating temperature (°C.) | initiating time (minutes) |
|---|---|---|---|---|---|---|---|
| example 1.15 | acrylonitrile | manganese dibutyldithiocarbamate and hydroquinone | 1 / 10 | yes | 300 | 70 | 70 |
| comparative example 1.22 | acrylonitrile | hydroquinone | 10 | yes | 300 | 70 | 35 |
| example 1.16 | styrene | manganese dibutyldithiocarbamate and hydroquinone | 1 / 10 | yes | 3000 | 70 | 200 or more |
| comparative example 1.23 | styrene | hydroquinone | 10 | yes | 3000 | 70 | 65 |

*(footnote): value (weight standard) against vinyl compound.

From the results of the Tables 1.1 to 1.8, the below-described 1.(a) to 1.(d) were confirmed.

1.(a) The polymerization inhibitors used in the examples including manganese dibutyldithiocarbamate, when compared with the polymerization inhibitors used in the comparative examples not including manganese dibutyldithiocarbamate, showed a high polymerization-inhibiting effect for various kinds of vinyl compounds.

1.(b) Even in the case where manganese dibutyldithiocarbamate is used alone, a sufficient polymerization-inhibiting effect is observed.

1.(c) If either one of hydroquinone or molecular oxygen jointly used with manganese dibutyldithiocarbamate, the polymerization-inhibiting effect further increases.

1.(d) If both of hydroquinone and molecular oxygen are jointly used with manganese dibutyldithiocarbamate, the polymerization-inhibiting effect is even further increased.

EXAMPLE 1.17

A continuous operation of an azeotropic separation of an aqueous acrylic acid solution was carried out, using a distillation column of a inner diameter 105 mm which was interiorly furnished with a stainless steel-made sieve tray having 50 steps at a step interval of 147 mm and equipped with a distillate tube at the upper part and a material supplying tube at the central part.

The polymerization-inhibiting ingredients used were manganese dibutyldithiocarbamate, hydroquinone, and molecular oxygen. Dibutyldithiocarbamate and hydroquinone were both introduced into the column from both positions of the feed step and the column top. Introduction from the feed step was carried out in form of adding followed by dissolving a defined amount into the undermentioned supplying material and, that from the column top was in form of adding followed by dissolving a defined amount into the undermentioned refluxing solution. A defined amount of molecular oxygen was supplied to a bottom part of the column. The each amount of polymerization inhibitors was 20 ppm of manganese dibutyldithiocarbamate and 200 ppm of hydroquinone against a boiling up amount of acrylic acid. Also, the poured oxygen amount was 0.3% by volume against a boiling up amount of acrylic acid.

The polymerization-inhibiting effect is confirmed by a pressure drop of the column inside, by flooding or by inspecting the column taken apart to pieces.

An acrylic acid containing 30% by weight of water and 2.5% by weight of acetic acid, which was obtained from a catalytic gas phase oxidation reaction of propylene, was used as a supplying material and methyl isobutyl ketone was used as a refluxing liquid, and distillation was carried out under the conditions of temperature at the column top 46° C., temperature at the column bottom 97° C., pressure at the column top 112 mmHg, amount of a supplying solution 10.56 liter/hr, and refluxing ratio (R/D)=0.92 (mole standard).

The liquid composition taken off from the column bottom under a stationary state was 97.0% by weight of acrylic acid, 0.5% by weight of acetic acid, and 2.5% by weight of others. The refluxing solution was used by recycling the distilled oil phase.

In operating for 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero. Here, the mdd value means a decreasing weight amount of a test piece and it is an indication for the presence or absence of corrosion of a device. Its unit is mg/(dm$^2$*day) and, according to its magnitude, the corrosion is evaluated by the following ①, ②, and ③ standards (the mdd values in the examples and comparative examples given below are the same).

① mdd<1: more than sufficient fitness for use
② 1≦mdd<5: fitness for use
③ mdd≧5: somewhat difficult for use

EXAMPLE 1.18

A continuous distillation operation methacrylic acid was carried out, using a distillation column of a inner diameter 105 mm which was interiorly furnished with a stainless steel-made sieve tray having 50 steps at a step interval of 147 mm and equipped with a distillate tube at the upper part and a material supplying tube at the central part.

The polymerization-inhibiting ingredients used were manganese dimethyldithiocarbamate, hydroquinone, and molecular oxygen. Manganese dimethyldithiocarbamate and hydroquinone were both introduced into the column from both positions of the feed step and the column top. Introduction from the feed step was carried out in form of adding followed by dissolving a defined amount into the undermentioned supplying material and that from the column top was in form of adding followed by dissolving a defined amount into the undermentioned refluxing solution. A definite amount of molecular oxygen was supplied to a bottom part of the column. Each amount of used polymerization-inhibiting ingredients was 20 ppm of manganese dimethyldithiocarbamate and 200 ppm of hydroquinone against a boiling up amount of methacrylic acid. Also, the poured oxygen amount was 0.3% by volume against a boiling up amount of methacrylic acid.

The polymerization-inhibiting effect is confirmed by a pressure drop of the column inside, by flooding, or by inspecting the column taken apart to pieces.

An aqueous methacrylic acid solution obtained from a catalytic gas phase oxidation reaction of isobutylene, which contains 37% by weight of methacrylic acid, 9.05% by weight of acetic acid, and 50% by weight of water, was subjected to an extracting operation by n-heptane with an extraction ratio of 1.3. The thus-obtained n-heptane phase containing 76.4% by weight of n-heptane, 21.8% by weight of methacrylic acid, and 1.3% by weight of acetic acid was used as a supplying material and distillated n-heptane was used as a refluxing solution. Distillation was carried out under the conditions of temperature at the column top 42° C., temperature at the column bottom 122° C., pressure at the column top 105 mmHg, and refluxing ratio=1.0 (weight standard).

The liquid composition taken off from the column bottom under a stationary state was 99.7% by weight of methacrylic acid.

In continuously operating for 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at an end of the operation and, the mdd value was zero.

EXAMPLE 1.19

The procedure of example 1.17 was repeated with the same device and conditions to carry out distillation of the aqueous acrylic acid solution, except that manganese diethyldithiocarbamate was used as manganese dithiocarbamate instead of manganese dibutyldithiocarbamate.

In continuously operating for about 14 days, a stable condition was always obtained and, after the operation was stopped, the results obtained by inspecting an inside of the distillation column did not show any occurrence of polymerization products.

Also, corrosion in a SUS 316 test piece (made by Nippon Yakin Kogyo Co., Ltd.), which was beforehand arranged in the column inside, was not recognized at an end of the operation and, the mdd value was zero.

EXAMPLE 1.20

The procedure of example 1.17 was repeated with the same device and conditions to carry out distillation of the aqueous acrylic acid solution, except that manganese diphenyldithiocarbamate was used as manganese dithiocarbamate instead of manganese dibutyldithiocarbamate.

In continuously operating for about 14 days, a stable condition was always obtained and, after the operation was stopped, the results obtained by inspecting an inside of the distillation column did not show any occurrence of polymerization products.

Also, corrosion in a SUS 316 test piece (made by Nippon Yakin Kogyo Co., Ltd.), which was beforehand arranged in the column inside, was not at all recognized at an end of the operation and, the mdd value was zero.

EXAMPLE 1.21

The procedure of example 1.17 was repeated with the same device and conditions to carry out distillation of the aqueous acrylic acid solution, except that copper dibutyldithiocarbamate, in an amount of 10 ppm against a boiling up amount of acrylic acid, was added as the polymerization-inhibiting ingredients as well.

In continuously operating for about 14 days, a stable condition was always obtained and, after the operation was stopped, the results obtained by inspecting an inside of the distillation column did not show any occurrence of polymerization products.

Also, corrosion in a SUS 316 test piece (made by Nippon Yakin Kogyo Co., Ltd.), which was beforehand arranged in the column inside, was not at all recognized at an end of the operation and, the mdd value was zero.

EXAMPLE 1.22

Using an evaporating vessel of an inside diameter 105 mm, a continuous operation was carried out to distill an acrylic acid solution.

The polymerization-inhibiting ingredients used were manganese dibutyldithiocarbamate, methoquinone, and molecular oxygen. Manganese dibutyldithiocarbamate and methoquinone were both introduced into the column from both positions of the feed and the condenser. Introduction was carried out in form of adding followed by dissolving a defined amount into the undermentioned supplying material. An definite amount of molecular oxygen was supplied to a bottom part of the column. The amounts of manganese dibutyldithiocarbamate and methoquinone used as polymerization inhibitors were respectively 12 ppm and 120 ppm against a boiling up amount of acrylic acid. Also, the poured oxygen amount was 0.3% by volume against a boiling up amount of acrylic acid.

The polymerization-inhibiting effect is confirmed by a pressure drop of the column inside or by inspecting the column taken apart to pieces.

A crude acrylic acid of purity 99.0% by weight containing 500 ppm of hydrazine was used as a supplying material and it was distilled under the conditions of temperature at the column top 63° C. and operating pressure 35 mmHg.

The distillate composition under a stationary condition was 99.9% by weight of acrylic acid.

In continuously operating for about 14 days, a stable condition was always obtained and, after the operation was stopped, the results obtained by inspecting an inside of the distillation column did not show any occurrence of polymerization products.

Also, corrosion in a SUS 316 test piece (made by Nippon Yakin Kogyo Co., Ltd.), which was beforehand arranged in the column inside, was not recognized at all after an end of the operation and, the mdd value was zero.

COMPARATIVE EXAMPLE 1.24

The procedure of example 1.17 was repeated with the same device and conditions to carry out distillation of the aqueous acrylic acid solution, except that copper dibutyldithiocarbamate instead of manganese dibutyldithiocarbamate was used in 20 ppm against a boiling up amount of acrylic acid.

After continuously operating for about 14 days, the results obtained by inspecting an inside of the distillation column slightly showed occurrence of a popcorn polymer. Also, corrosion in a SUS 316 test piece (made by Nippon Yakin Kogyo Co., Ltd.), which was beforehand arranged in the column inside, was recognized after an end of the operation, and the test piece showed the mdd value of 5.0.

From these results, when copper dithiocarbamate is used instead of manganese dithiocarbamate, decrease of the polymerization-inhibiting effect is seen and corrosion of the device takes place.

COMPARATIVE EXAMPLE 1.25

The procedure of example 1.17 was repeated with the same device and conditions to carry out distillation of the aqueous acrylic acid solution, except that manganese acetate instead of manganese dibutyldithiocarbamate was used in 20 ppm against a boiling up amount of acrylic acid.

As a result, pressure drop of the column inside was recognized after 2 days from initiation of operation, and continuation of the operation became difficult. Thus, the operation was stopped and, for inspection, the column was taken apart to pieces and thereby, formation of a sticky polymer was found in the column.

From the result, if a manganese salt other than manganese dithiocarbamate is used, decrease of the polymerization-inhibiting effect was confirmed in distillation.

EXAMPLE 2.1

An acrylic acid solution was prepared by adding tetrabutylthiuram disulfide (hereinafter, abbreviated to TBTDS) as a polymerization inhibitor in a proportion of 2 ppm to purified acrylic acid. The acrylic acid solution, 5 ml, was taken into a 20 ml test tube to dissolve oxygen in the acrylic acid solution by bubbling air for 1 minute with a stream amount of 30 ml/minute, and then, the test tube was sealed. This test tube was immersed in an oil bath maintained at 130° C. and a polymerization-initiating time of acrylic acid was measured. But this time is a time of from immersing a test tube in an oil bath until getting turbidity in the solution sealed in the test tube. Results are shown in the following Table 2.1

COMPARATIVE EXAMPLES 2.1 AND 2.2

The polymerization-initiating time of acrylic acid was measured in a way similar to the example 2.1 except that 50 ppm of hydroquinone or methoquinone was added as a polymerization inhibitor instead of TBTDS. Results obtained are shown in the following Table 2.1

EXAMPLE 2.2

The polymerization-initiating time of acrylic acid was measured in a way similar to the example 2.1 except that 2 ppm of TBTDS and 1 ppm of manganese acetate were added as polymerization inhibitors. Results obtained are shown in the following Table 2.1

EXAMPLE 2.3

The polymerization-initiating time of acrylic acid was measured in a way similar to the example 2.1 except that 2 ppm of TBTDS, 1 ppm of manganese acetate, and 50 ppm of hydroquinone were added as polymerization inhibitors. Results obtained are shown in the following Table 2.1

COMPARATIVE EXAMPLES 2.3 AND 2.4

The polymerization-initiating time of acrylic acid was measured in a way similar to the example 2.2 or 2.3 except that TBTDS was not at all added as a polymerization inhibitor. Results obtained are shown in the following Table 2.1

COMPARATIVE EXAMPLE 2.5

The polymerization-initiating time of acrylic acid was measured in a way similar to the example 2.1 except that 1 ppm of copper dibutyldithiocarbamate and 50 ppm of hydroquinone were added as polymerization inhibitors in stead of TBTDS. Results obtained are shown in the following Table 2.1

EXAMPLE 2.4

The polymerization-initiating time of acrylic acid was measured in a way similar to the example 2.1 except that 2 ppm of TBTDS and 1 ppm of manganese acetate were added as polymerization inhibitors and that bubbling of a nitrogen gas instead of air was carried out to remove oxygen in the acrylic acid solution. Results obtained are shown in the following Table 2.2 except that TBTDS was not at all added as a polymerization inhibitor. Results obtained are shown in the following Table 2.2.

TABLE 2.1

|  | polymerization inhibitor | | oxygen in acrylic acid solution | heating temperature (°C.) | polymerization initiating time (minutes) |
|---|---|---|---|---|---|
|  | kind | adding amount (ppm)* | | | |
| example 2.1 | TBTDS | 2 | yes | 130 | 17 |
| comparative example 2.1 | hydroquinone | 50 | yes | 130 | 5 |
| comparative example 2.2 | methoquinone | 50 | yes | 130 | 5 |
| example 2.2 | TBTDS and manganese acetate | 2<br>1 | yes | 130 | 70 |
| example 2.3 | TBTDS, manganese acetate, and hydroquinone | 2<br>1<br>50 | yes | 130 | 200 or more |
| comparative example 2.3 | manganese acetate | 1 | yes | 130 | 50 |
| comparative example 2.4 | manganese acetate and hydroquinone | 1<br>50 | yes | 130 | 81 |
| comparative example 2.5 | copper dibutyldithiocarbamate and hydroquinone | 1<br>50 | yes | 130 | 50 |

*(footnote): value (weight standard) against acrylic acid.

TABLE 2.2

|  | polymerization inhibitor | | oxygen in acrylic acid solution | heating temperature (°C.) | polymerization initiating time (minutes) |
|---|---|---|---|---|---|
|  | kind | adding amount (ppm)* | | | |
| example 2.4 | TBTDS and manganese acetate | 2<br>1 | none | 130 | 27 |
| example 2.5 | TBTDS, manganese acetate, and hydroquinone | 2<br>1<br>50 | none | 130 | 72 |
| comparative example 2.6 | manganese acetate | 1 | none | 130 | 17 |
| comparative example 2.7 | manganese acetate and hydroquinone | 1<br>50 | none | 130 | 24 |

*(footnote): value (weight standard) against acrylic acid.

EXAMPLE 2.5

The polymerization-initiating time of acrylic acid was measured in a way similar to the example 2.1 except that 2 ppm of TBTDS, 1 ppm of manganese acetate, and 50 ppm of hydroquinone were added as polymerization inhibitors and that bubbling of a nitrogen gas instead of air was carried out to remove oxygen in the acrylic acid solution. Results obtained are shown in the following Table 2.2

COMPARATIVE EXAMPLES 2.6 AND 2.7

The polymerization-initiating time of acrylic acid was measured in a way similar to the example 2.4 or 2.5

EXAMPLES 2.6 TO 2.10 AND COMPARATIVE EXAMPLES 2.8 TO 2.14

The procedure of example 2.1 was repeated except that methacrylic acid was used instead of acrylic acid, the heating temperature was changed to 160° C., and the kind and adding amount of polymerization-inhibitors and the kind of a bubbling gas into the acid solution were varied as shown in the following Tables 2.3 and 2.4, whereby the polymerization-initiating time of methacrylic acid was measured and the results are shown in the Tables 2.3 and 2.4.

TABLE 2.3

|  | polymerization inhibitor | | oxygen in acrylic acid solution | heating temperature (°C.) | polymerization initiating time (minutes) |
|---|---|---|---|---|---|
|  | kind | adding amount (ppm)* | | | |
| example 2.6 | TBTDS | 2 | yes | 160 | 22 |
| comparative example | hydroquinone | 50 | yes | 160 | 5 |

TABLE 2.3-continued

| | polymerization inhibitor | | oxygen | | polymerization |
| | kind | adding amount (ppm)* | in acrylic acid solution | heating temperature (°C.) | initiating time (minutes) |
|---|---|---|---|---|---|
| comparative example 2.8 | methoquinone | 50 | yes | 160 | 5 |
| example 2.7 | TBTDS and manganese acetate | 2 1 | yes | 160 | 83 |
| example 2.8 | TBTDS, manganese acetate, and hydroquinone | 2 1 50 | yes | 160 | 200 or more |
| comparative example 2.9 | manganese acetate | 1 | yes | 160 | 63 |
| comparative example 2.10 | manganese acetate and hydroquinone | 1 50 | yes | 160 | 102 |
| comparative example 2.11 | copper dibutyldithiocarbamate and hydroquinone | 1 50 | yes | 160 | 50 |
| comparative example 2.12 | | | | | |

*(footnote): value (weight standard) against methacrylic acid.

TABLE 2.4

| | polymerization inhibitor | | oxygen | | polymerization |
| | kind | adding amount (ppm)* | in acrylic acid solution | heating temperature (°C.) | initiating time (minutes) |
|---|---|---|---|---|---|
| example 2.9 | TBTDS and manganese acetate | 2 1 | none | 160 | 37 |
| example 2.10 | TBTDS, manganese acetate, and hydroquinone | 2 1 50 | none | 160 | 80 |
| comparative example 2.13 | manganese acetate | 1 | none | 160 | 20 |
| comparative example 2.14 | manganese acetate and hydroquinone | 1 50 | none | 160 | 29 |

*(footnote): value (weight standard) against methacrylic acid.

EXAMPLES 2.11 TO 2.15 AND COMPARATIVE EXAMPLES 2.15 TO 2.19

The procedure of example 2.1 was repeated except that the kind of vinyl compounds, the kind and adding amount of polymerization-inhibitors, the kind of bubbling gas into the vinyl compound solution, and the heating temperature, were varied as shown in the following Tables 2.5 and 2.6, whereby the polymerization-initiating time of vinyl compounds was measured. But, in the examples 2.13 to 2.15 and comparative examples 2.17 to 2.19, a polymerization initiator (azoisobutyronitrile; abbreviated to AIBN in the Tables 2.5 and 2.6) was added in amounts as shown in the Tables 2.5 and 2.6 besides of the polymerization-inhibitors.

The results obtained are shown in the Tables 2.5 and 2.6.

TABLE 2.5

| | vinyl compound | polymerization inhibitor | | adding amount of AIBN (ppm)* | oxygen in vinyl compound solution | heating temperature (°C.) | polymerization initiating time (minutes) |
| | | kind | adding amount (ppm)* | | | | |
|---|---|---|---|---|---|---|---|
| example 2.11 | methyl acrylate | TBTDS and hydroquinone | 2 10 | none | yes | 100 | 133 |
| comparative example 2.15 | methyl acrylate | hydroquinone | 10 | none | yes | 100 | 80 |
| example 2.12 | octyl acrylate | TBTDS and hydroquinone | 2 10 | none | yes | 70 | 149 |
| comparative example 2.16 | octyl acrylate | hydroquinone | 10 | none | yes | 70 | 90 |
| example 2.13 | methyl methacrylate | TBTDS and hydroquinone | 2 10 | 200 | yes | 80 | 160 |
| comparative example 2.17 | methyl methacrylate | hydroquinone | 10 | 200 | yes | 80 | 110 |

*(footnote): value (weight standard) against vinyl compound.

TABLE 2.6

| | vinyl compound | polymerization inhibitor kind | polymerization inhibitor adding amount (ppm)* | adding amount of AIBN (ppm)* | oxygen in vinyl compound solution | heating temperature (°C.) | polymerization initiating time (minutes) |
| --- | --- | --- | --- | --- | --- | --- | --- |
| example 2.14 | acrylonitrile | TBTDS and hydroquinone | 2 10 | 300 | yes | 70 | 52 |
| comparative example 2.18 | acrylonitrile | hydroquinone | 10 | 300 | yes | 70 | 35 |
| example 2.15 | styrene | TBTDS and hydroquinone | 2 10 | 3000 | yes | 70 | 97 |
| comparative example 2.19 | styrene | hydroquinone | 10 | 3000 | yes | 70 | 65 |

*(footnote): value (weight standard) against vinyl compound.

EXAMPLE 2.16

A continuous operation of an azeotropic separation of an aqueous acrylic acid solution was carried out, using a distillation column of a inner diameter 105 mm which was interiorly furnished with a stainless steel-made sieve tray having 50 steps at a step interval of 147 mm and equipped with a distillate tube at the upper part and a material supplying column at the central part, and also, using TBTDS, acetate manganese, and hydroquinone as polymerization inhibitors.

An aqueous acrylic acid solution containing 66.5% by weight of acrylic acid, 30% by weight of water and 2.5% by weight of acetic acid, which was obtained from a catalytic gas phase oxidation reaction of propylene, was supplied to the central step of the distillation column. Methyl isobutyl ketone was used as an azeotropic solvent. An distillate liquid was separated into an oil phase and a water phase, and the water phase was taken off and the oil phase was used as a refluxing liquid. Distillation was carried out under the conditions of temperature at the column top 46° C., temperature at the column bottom 97° C., pressure at the column top 112 mmHg, amount of a supplying solution 10.56 liter/hr, and refluxing ratio (R/D)=0.92 (mole standard). During the distillation, acetate manganese, TBTDS and hydroquinone were introduced from the column top into the column, in form of adding and dissolving the acetate manganese into the distilled water phase, and adding and dissolving the TBTDS and hydroquinone into the refluxing liquid. Also, molecular oxygen was supplied to a bottom part of the column. The each amount of polymerization inhibitors was 18 ppm of TBTDS, 11 ppm of manganese acetate, and 200 ppm of hydroquinone against a boiling up amount of acrylic acid. Also, the poured oxygen amount was 0.3% by volume against a boiling up amount of acrylic acid. The liquid composition taken off from the column bottom under a stationary state was 97.0% by weight of acrylic acid, 0.5% by weight of acetic acid, and 2.5% by weight of others.

In operating for 14 days under these conditions, a stable state was always obtained without matters of a pressure drop of the column inside, flooding, etc. After the operation was stopped, the results obtained from inspecting an inside of the distillation column did not show any occurrence of polymerization.

Also, in this experiment, in order to examine corrosion of the device materials, a SUS 316 test piece (made by Nippon Yakin Kogyo Co., Ltd.) was beforehand arranged in the column inside. When the test piece was taken out at the end of operation, its corrosion was not recognized at all, and the mdd value was zero.

EXAMPLE 2.17

A continuous operation for distillation of methacrylic acid was carried out, using a distillation column of a inner diameter 105 mm which was interiorly furnished with a stainless steel-made sieve tray having 50 steps at a step interval of 147 mm and equipped with a distillate tube at the upper part and a material supplying tube at the central part, and also, using TBTDS, acetate manganese, and hydroquinone as polymerization inhibitors.

An aqueous methacrylic acid solution obtained by collecting gas products in a catalytic gas phase oxidation reaction of isobutylene was subjected to an extracting operation by n-heptane. The thus-obtained n-heptane phase containing 76.4% by weight of n-heptane, 21.8% by weight of methacrylic acid, and 1.3% by weight of acetic acid was used as a material supplied to the distillation column. This material was supplied from the material supplying tube to the central step of the distillation column, and distillation was carried out under the conditions of temperature at the column top 42° C., temperature at the column bottom 122° C., pressure at the column top 105 mmHg, and refluxing ratio=1.0 (weight standard). During the distillation, acetate manganese, TBTDS and hydroquinone were introduced from the column top into the column, in form of adding and dissolving the acetate manganese into water, and adding and dissolving the TBTDS and hydroquinone into the refluxing liquid. Also, molecular oxygen was supplied to a bottom part of the column. The each amount of polymerization inhibitors was 18 ppm of TBTDS, 11 ppm of manganese acetate, and 200 ppm of hydroquinone against a boiling up amount of methacrylic acid. Also, the poured oxygen amount was 0.3% by volume against a boiling up amount of methacrylic acid. The liquid composition taken off from the column bottom under a stationary state was 99.7% by weight of methacrylic acid.

In operating for 14 days under these conditions, a stable state was always obtained without matters of a pressure drop of the column inside, flooding, etc. After the operation was stopped, the results obtained from inspecting an inside of the distillation column did not show any occurrence of polymerization.

Also, in this experiment, in order to examine corrosion of the device materials, a SUS 316 test piece (made by Nippon Yakin Kogyo Co., Ltd.) was beforehand arranged in the column inside. When the test piece was taken out at the end of operation, its corrosion was not recognized at all, and the mdd value was zero.

EXAMPLE 2.18

A continuous operation was carried out to distill an acrylic acid solution, using an evaporating vessel of an inside diameter 105 mm and as polymerization inhibitors, TBTDS, manganese acetate, and methoquinone.

A crude acrylic acid of purity 99.0% by weight containing 500 ppm of hydrazine was used as a supplying material and it was distilled under the conditions of temperature at the column top 63° C. and operating pressure 35 mmHg. During the distillation, TBTDS, acetate manganese, and methoquinone in the amounts respectively corresponding to 11 ppm, 7 ppm, and 120 ppm against a boiling up amount of acrylic acid were supplied to the distillation column together with the supplying material, in form of adding and dissolving these TBTDS, acetate manganese, and methoquinone into the supplying material. Also, molecular oxygen was supplied to a bottom part of the column in the amount corresponding to 0.3% by volume against a boiling up amount of acrylic acid. The liquid composition taken off from the column bottom under a stationary state was 99.9% by weight of acrylic acid.

In operating for 14 days under these conditions, a stable state was always obtained without matters of a pressure drop of the column inside, flooding, etc. After the operation was stopped, the results obtained from inspecting an inside of the distillation column did not show any occurrence of polymerization.

Also, corrosion of a SUS 316 test piece (made by Nippon Yakin Kogyo Co., Ltd.) beforehand arranged in the column inside was not at all recognized at the end of operation, and the mdd value was zero.

EXAMPLE 2.19

The procedure of example 2.16 was repeated with the same device and conditions to carry out distillation of the aqueous acrylic acid solution, except that copper acetate instead of manganese acetate was used.

In operating for about 14 days under these conditions, a stable state was always obtained without matters of a pressure drop of the column inside, flooding, etc. But, when a SUS 316 test piece (made by Nippon Yakin Kogyo Co., Ltd.) beforehand arranged in the column inside was examined, it showed the mdd value of 5.0. From the results, it was confirmed that corrosion of the device becomes slightly large by joint use of TBTDS and copper acetate, compared with joint use of TBTDS and manganese acetate.

From the results seen above, the following findings, 2.(a) to 2.(e), were confirmed.

2.(a) A polymerization-inhibiting effect is obtained even when the thiuram compound represented by the general formula (1) of the present invention is used alone.

2.(b) If a manganese salt or a copper salt is jointly used in addition to the thiuram compound represented by the general formula (1) of the present invention, the polymerization-inhibiting effect increases.

2.(c) If hydroquinone and/or methoquinone are jointly used in addition to the above 2.(b) composition, the polymerization-inhibiting effect further increases.

2.(d) In the example in which the thiuram compound represented by the general formula (1) of the present invention was used, compared with the comparative example in which hydroquinone or the like was used instead of the thiuram compound, the polymerization-inhibiting effect on the vinyl compounds is high.

2.(e) In a case where the thiuram compound represented by the general formula (1) of the present invention is jointly used with a manganese salt, fewer corrosion of a device is found in addition to a superior polymerization-inhibiting effect, and a continuous operation in a long period of time of a device for producing vinyl compounds becomes possible.

EXAMPLE 3.1

A continuous operation of an azeotropic separation of an aqueous acrylic acid solution was carried out, using a distillation column of a inner diameter 105 mm which was interiorly furnished with a stainless steel-made sieve tray having 50 steps at a step interval of 147 mm and equipped with a distillate tube at the upper part and a material supplying tube at the central part.

The polymerization inhibitors used were manganese acetate, copper dibutyldithiocarbamate, hydroquinone, and molecular oxygen. Copper dibutyldithiocarbamate was introduced into the column from the top in form of adding followed by dissolving the defined amount into the undermentioned refluxing solution. Manganese acetate was introduced into the column from both positions of the feed step and the column top, its introduction from the feed step being carried out in form of adding followed by dissolving the defined amount into the undermentioned supplying material and, that from the column top being in form of adding followed by dissolving the defined amount into water. Hydroquinone was introduced into the column from both positions of the feed step and the column top, its introduction from the feed step being carried out in form of adding followed by dissolving the defined amount into the undermentioned supplying material and, that from the column top being in form of adding followed by dissolving the defined amount into the undermentioned refluxing solution. A defined amount of molecular oxygen was supplied to a bottom part of the column. The each amount of polymerization inhibitors was 30 ppm of manganese acetate, 20 ppm of copper dibutyldithiocarbamate and 200 ppm of hydroquinone against a boiling up amount of acrylic acid. Also, the weight ratio of manganese atom to copper atom (Mn/Cu) in this case was 3.5. Also, the poured oxygen amount was 0.3% by volume against a boiling up amount of acrylic acid.

The polymerization-inhibiting effect is confirmed by a pressure drop of the column inside, by flooding or by inspecting the column taken apart to pieces.

An acrylic acid containing 30% by weight of water and 2.5% by weight of acetic acid, which was obtained from a catalytic gas phase oxidation reaction of propylene, was used as a supplying material and methyl isobutyl ketone was used as a refluxing liquid, and distillation was carried out under the conditions of temperature at the column top 46° C., temperature at the column bottom 97° C., pressure at the column top 112 mmHg, amount of a supplying solution 10.56 liter/hr, and refluxing ratio (R/D)=0.92 (mole standard).

The liquid composition taken off from the column bottom under a stationary state was 97.0% by weight of acrylic acid, 0.5% by weight of acetic acid, and 2.5% by weight of others. The refluxing solution was used by recycling the distilled oil phase.

The distillation percent of acetic acid is 85.2% under the forementioned stationary conditions, and the present distillation experiment had a condition which separates acetic acid together with water from an acrylic acid containing 30% by weight of water and 2.5% by weight of acetic acid.

In continuously operating for about 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero.

EXAMPLE 3.2

A continuous distillation operation was carried out in a way similar to the example 3.1 except that acrylic acid was changed to methacrylic acid. But an aqueous methacrylic acid solution obtained from a catalytic gas phase oxidation reaction of isobutylene, which contains 37% by weight of methacrylic acid, 9.07% by weight of acetic acid, and 50% by weight of water, was subjected to an extracting operation by n-heptane with an extraction ratio of 1.3. The thus-obtained n-heptane phase containing 76.4% by weight of n-heptane, 21.8% by weight of methacrylic acid, and 1.3% by weight of acetic acid was used as a supplying material. Distillation was carried out under the conditions of temperature at the column top 42° C., temperature at the column bottom 122° C., pressure at the column top 105 mmHg, and refluxing ratio=1.0 (weight standard).

In continuously operating for about 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero.

EXAMPLE 3.3

A continuous distillation operation was carried out in a way similar to the example 3.1 except that manganese octanate instead of manganese acetate was used as a manganese salt. But the use amount of manganese octanate was 60 ppm against a boiling up amount of acrylic acid. Also, the weight ratio of manganese atom to copper atom (Mn/Cu) in this case was 3.5.

In continuously operating for about 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero.

EXAMPLE 3.4

A continuous distillation operation was carried out in a way similar to the example 3.1 except that potassium permanganate instead of manganese acetate was used as a manganese salt. But the use amount of potassium permanganate was 30 ppm against a boiling up amount of acrylic acid. Also, the weight ratio of manganese atom to copper atom (Mn/Cu) in this case was 3.8.

In continuously operating for about 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero.

EXAMPLE 3.5

A continuous distillation operation was carried out in a way similar to the example 3.1 except that copper dimethyldithiocarbamate instead of copper dibutyldithiocarbamate was used as a copper dithiocarbamate. But the use amount of copper dimethyldithiocarbamate was 20 ppm against a boiling up amount of acrylic acid. Also, the weight ratio of manganese atom to copper atom (Mn/Cu) in this case was 3.2.

In continuously operating for about 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero.

EXAMPLE 3.6

A continuous distillation operation was carried out in a way similar to the example 3.1 except that methoquinone was used instead of hydroquinone. But the use amount of methoquinone was 200 ppm against a boiling up amount of acrylic acid.

In continuously operating for about 14 days under these conditions, a stable state was always obtained and, after the operation was stopped, the results obtained from inspecting an inside of the distillation column did not show any occurrence of polymerization.

Also, corrosion in a SUS 316 test piece (made by Nippon Yakin Kogyo Co., Ltd.), which was beforehand arranged in the column inside, was not recognized at the end of operation, and the mdd value was zero.

EXAMPLE 3.7

The procedure of example 3.1 was repeated with the same device and conditions to carry out distillation of the aqueous acrylic acid solution, except that the use amount of manganese acetate only was increased to 100 ppm and that the weight ratio between manganese atom and copper atom (Mn/Cu) was 12. As a result, after 5 days from initiation of operation, pressure drop of the column inside was very slightly recognized. From the result, if the weight ratio between manganese atom and copper atom (Mn/Cu) is too high, decrease of the polymerization-inhibiting effect was confirmed.

COMPARATIVE EXAMPLE 3.1

The procedure of example 3.1 was repeated with the same device and conditions to carry out distillation of the aqueous acrylic acid solution, except that manganese acetate was not at all used. After continuously operating for about 14 days, the results obtained by inspecting an inside of the distillation column slightly showed occurrence of a popcorn polymer. Also, corrosion in a SUS 316 test piece (made by Nippon Yakin Kogyo Co., Ltd.), which was beforehand arranged in the column inside, was recognized, and the test piece showed the mdd value of 5.0.

From these results, when a copper dithiocarbamate, a phenol compound, and molecular oxygen are only used without a manganese salt, decrease of the polymerization-inhibiting effect is seen and corrosion of the device takes place.

COMPARATIVE EXAMPLE 3.2

The procedure of example 3.1 was repeated with the same device and conditions to carry out distillation of the aqueous acrylic acid solution, except that copper dibutyldithiocarbamate was not used. As a result, pressure drop of the column inside was recognized after 2 days from initiation of operation, and continuation of the operation became difficult. Thus, the operation was stopped and, for inspection, the column was taken apart to pieces and thereby, formation of a sticky polymer was found in the column. From the result, if a manganese salt other than a manganese dithiocarbamate, a phenol compound, and molecular oxygen are only used without use of a copper dithiocarbamate, decrease of the polymerization-inhibiting effect was confirmed in distillation.

What is claimed are:

1. A composition comprising a vinyl monomer and an effective amount of a polymerization inhibitor, said polymerization inhibitor comprising a manganese dithiocarbamate having a nitrogen atom bonded with two hydrocarbon groups of identical or different kinds selected from the group consisting of a methyl, an ethyl, a propyl, a butyl, and a phenyl group, wherein said propyl or butyl group may be either a straight chain type or a branched type.

2. The composition as claimed in claim 1, further comprising a benzene derivative as an additional polymerization inhibitor, said benzene derivative being at least one selected from the group consisting of hydroquinone, p-methoxyphenol, cresol, phenol, tertiary-butylcatecol, diphenylamine, phenothiazine and methylene blue.

3. The composition as claimed in claim 2, wherein the vinyl monomer is any one selected from the group consisting of acrylic acid, methacrylic acid, an acrylic acid ester, a methacrylic acid ester, acrylonitrile, and styrene.

4. A polymerization-inhibiting method for a vinyl monomer, which comprises adding, as an effective polymerization-inhibiting component, a manganese dithiocarbamate having a nitrogen atom bonded with two hydrocarbon groups of identical or different kinds selected from the group consisting of a methyl, an ethyl, a propyl, a butyl, and a phenyl group, wherein said propyl or butyl group may be either a straight chain type or a branched type.

5. A polymerization-inhibiting method for a vinyl monomer as claimed in claim 4, which further comprises adding to said vinyl monomer and said manganese dithiocarbamate at least one benzene derivative selected from the group consisting of hydroquinone, p-methoxyphenol, cresol, phenol, tertiary-butylcatechol, diphenylamine, phenothiazine and methylene blue as an additional polymerization inhibitor.

6. A polymerization-inhibiting method for a vinyl monomer as claimed in claim 4, wherein said method is carried out in the presence of molecular oxygen.

7. A polymerization-inhibiting method for a vinyl monomer as claimed in claim 5, wherein said method is carried out in the presence of molecular oxygen.

8. A polymerization-inhibiting method for a vinyl monomer as claimed in claim 7, wherein the vinyl monomer is any one selected from the group consisting of acrylic acid, methacrylic acid, an acrylic acid ester, a methacrylic acid ester, acrylonitrile, and styrene.

9. A polymerization-inhibiting method for a vinyl monomer, which comprises adding a copper dithiocarbamate and a manganese salt to the vinyl monomer as polymerization-inhibitors, wherein the ratio of manganese to copper is at least 1.

10. A polymerization-inhibiting method for a vinyl monomer as claimed in claim 9, which further comprises adding at least one benzene derivative selected from the group consisting of hydroquinone, p-methoxyphenol, cresol, phenol, tertiary-butylcatechol, diphenylamine, phenothiane and methylene blue in combination with said copper dithiocarbamate and said manganese salt as an additional polymerization inhibitor.

11. A polymerization-inhibiting method for a vinyl monomer as claimed in claim 9, wherein said method is carried out in the presence of molecular oxygen.

12. A polymerization-inhibiting method for a vinyl monomer as claimed in claim 10, wherein said method is carried out in the presence of molecular oxygen.

13. A polymerization-inhibiting method for a vinyl monomer as claimed in claim 12, wherein the vinyl monomer is any one selected from the group consisting of acrylic acid, methacrylic acid, an acrylic acid ester, a methacrylic acid ester, acrylonitrile and styrene.

14. A polymerization-inhibiting method for a vinyl monomer as claimed in claims 9, wherein said manganese salt is other than a manganese dithiocarbamate.

15. A polymerization-inhibiting method for a vinyl monomer as claimed in claim 14, wherein said manganese salt is at least one selected from the group consisting of a manganese carboxylate salt and a manganese inorganic acid salt.

16. A polymerization-inhibiting method for a vinyl monomer as claimed in claim 13, wherein said manganese salt is other than a manganese dithiocarbamate.

17. A polymerization-inhibiting method for a vinyl monomer as claimed in claim 16, wherein said manganese salt is at least one selected from the group consisting of a manganese carboxylate salt and a manganese inorganic acid salt.

* * * * *